United States Patent [19]

Vacek

[11] 4,307,031
[45] Dec. 22, 1981

[54] PREPARATION OF A DITHIODIBENZOATE, DITHIOCARBONATE, TRITHIOCARBONATE MIXTURE

[75] Inventor: Lubomir Vacek, Toledo, Ohio

[73] Assignee: The Sherwin-Williams Company, Cleveland, Ohio

[21] Appl. No.: 150,936

[22] Filed: May 19, 1980

Related U.S. Application Data

[63] Continuation-in-part of Ser. No. 946,397, Sep. 27, 1978, abandoned, which is a continuation of Ser. No. 748,142, Dec. 6, 1976, abandoned, which is a continuation of Ser. No. 572,040, Apr. 28, 1975, abandoned.

[51] Int. Cl.$^3$ ............... C07C 153/043; C07C 149/40
[52] U.S. Cl. ........................... 260/455 R; 260/455 B; 568/21; 560/17
[58] Field of Search .......................... 560/17; 568/21; 260/455 B, 455 R

[56] References Cited

U.S. PATENT DOCUMENTS 3,652,632  3/1972  Vacek ............................ 260/455 B Primary Examiner—John M. Ford
Assistant Examiner—Robert C. Whittenbaugh
Attorney, Agent, or Firm—John C. Purdue

[57] ABSTRACT

A method for producing a mixture of a dithiodibenzoate, a dithiocarbonate, and a trithiocarbonate, is disclosed. The method includes diazotizing an amine having the formula

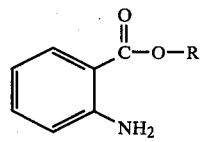

where R is hydrogen, or an alkyl group having not more than 4 carbon atoms, and coupling the resulting diazonium with at least 1 gram-mole of carbon disulfide per gram-mole of the diazonium in the presence of a copper catalyst. Under appropriate conditions, which include a reaction temperature in the range of 10°–32° C., sufficient time for full coupling to occur, and dissolving of the $CS_2$ in a suitable water-miscible solvent such as methanol, coupling to said mixture readily occurs. The coupling products are then dissolved and removed by use of a water-immiscible inert solvent. According to the invention, the surface area of copper must be at least 2000 square centimeters per gram-mole of the diazonium reactant to adequately catalyze coupling; larger areas up to substantially 3000 square centimeters per gram-mole are preferred, a greater area than 3000 square centimeters having no effect. The products of the coupling reaction can be converted to saccharin or 2,2'-dithiodibenzoic acid, useful as an intermediate in the production of compounds such as 1,2-benzisothiazoline-3-one, a fungicide and bactericide.

13 Claims, No Drawings

PREPARATION OF A DITHIODIBENZOATE, DITHIOCARBONATE, TRITHIOCARBONATE MIXTURE

REFERENCE TO RELATED APPLICATIONS

This is a continuation-in-part of application Ser. No. 946,397, filed Sept. 27, 1978, now abandoned, as a continuation of application Ser. No. 748,142, filed Dec. 6, 1976, now abandoned, which in turn was a continuation of application Ser. No. 572,040, filed Apr. 28, 1975, now abandoned.

BACKGROUND OF THE INVENTION

1. Field of the Invention

This invention relates to a method for the preparation of a mixture of a dithiodibenzoate, a dithiocarbonate, and a trithiocarbonate. These compounds are useful as intermediates for the production of saccharin or saccharin salts* and can undergo hydrolysis followed by oxidation to produce 2,2'-dithiodibenzoic acid, useful as an intermediate in the production of compounds such as 1,2-benzisothiazoline-3-one** which has utility as a fungicide and bactericide.
*See, for example, U.S. Pat. Nos. 2,667,503 and 3,325,475.
**See, for example, British Pat. Nos. 918,869 and 884,541.

2. Description of the Prior Art

The prior art describes methods of diazotizing an aminobenzoic acid ester or thio ester, and reacting the resulting diazonium salt with such compounds as disulfide salts, xanthate salts and trithiocarbonate salts, to produce organic xanthates, di-and trithiocarbonates, and alkylene-dixanthates.*
*See, for example, U.S. Pat. No. 3,652,632.

The reaction of diazonium compounds with $CS_2$ has not been extensively studied. A few academic works have mentioned $CS_2$ in connection with attempts to explain the mechanism of decomposition and some reactions of aromatic diazonium compounds. Also, the reaction of arylradicals (which had been produced from corresponding aryldiazonium fluoroborates by the action of NaI) with $CS_2$ to produce various diaryldisulfides has been discussed.*
**See, for example, Hurtley and Smiles, J. Chem. Soc., (1926) pp. 1821-28, and Hodgson, J. Chem. Soc., (1948) pp. 348-54.
***Reactivity of Carbon Disulfide with Aryl Radicals, J. Org. Chem., 41, (1976) pp. 2639-40.

BRIEF DESCRIPTION OF THE INVENTION

The instant invention is based upon the discovery of a method for producing a mixture of a dithiodibenzoate, a dithiocarbonate, and a trithiocarbonate. The method includes diazotizing an amine having the formula

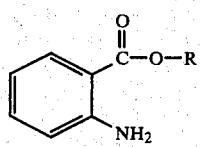

where R is hydrogen, or an alkyl group having from 1 to 4 carbon atoms, and then reacting the resulting diazonium salt in the presence of metallic copper with an equimolecular quantity of $CS_2$ dissolved in a water-miscible solvent, such as methanol.

When the diazonium-$CS_2$ coupling is carried out under appropriate temperature conditions, i.e., in the range of 10-32° *, dithiodibenzoates, dithiocarbonates, and trithiocarbonates are produced. These products can be converted to saccharin or can be base hydrolyzed and then oxidized to 2,2'-dithiodibenzoic acid, which is a useful intermediate in the manufacture of 1,2-benzisothiazoline-3-one, a fungicide/bactericide.
*All temperatures herein and in the claims are expressed in degrees celsius.

Accordingly, it is an object of this invention to provide an improved method for producing a dithiodibenzoate, dithiocarbonate, trithiocarbonate mixture.

Other objects and advantages will be apparent from the following detailed description, which is intended only to illustrate and disclose but in no way to limit the invention as defined in the claims appended hereto.

DETAILED DESCRIPTION OF THE INVENTION

This invention relates to an improved method for producing a starting material useful in the manufacture of saccharin and such compounds as 2,2'-dithiodibenzoic acid, which is used as a reactant in the production of 1,2-benzisothiazoline-3-one, a fungicide/bactericide. The method comprises the steps of diazotizing an amine having the formula

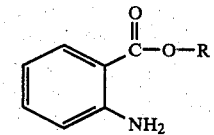

where R is hydrogen, or a methyl, ethyl, propyl, isopropyl, butyl or sec-butyl group, to form a diazonium salt, and then coupling the diazonium with carbon disulfide in the presence of a copper catalyst to produce a mixture of a dithiodibenzoate, a dithiocarbonate, and a trithiocarbonate. The ratio between specific end products is a function of numerous factors; among these are the identity of the alkyl group R, the time allowed for coupling to take place, and the temperature at which the reaction mixture is maintained.

Diazotization of the amine according to the method of this invention can be illustrated as follows:

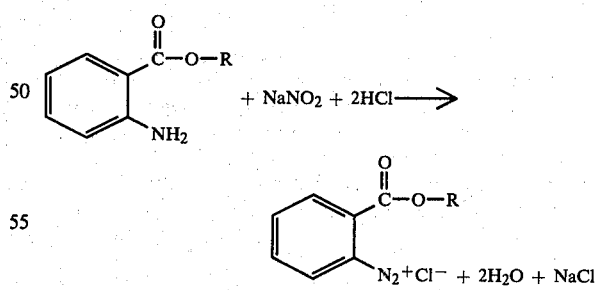

The diazonium thus formed is then reacted with $CS_2$ in the presence of copper. The reaction is believed to proceed because of the generation of free radicals from diazonium cations, due to electron donation by the copper or by cuprous ions. The o-alkoxycarbonylphenyl radicals so generated then react with $CS_2$, generating a gas (a mixture of COS, $H_2S$, and $CS_2$ vapors together with $N_2$ from the radical formation), and yielding a dithiodibenzoate having the formula

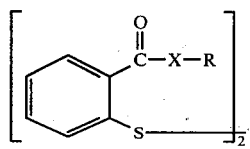

and a thiocarbonate having the formula

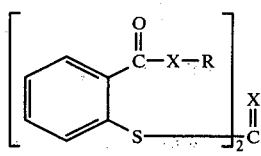

where X is oxygen or sulfur, and R is hydrogen or an alkyl group having from 1 to 4 carbon atoms. In addition to the above desired products, small, variable amounts of benzoate, o-chlorobenzoate or salicylate, diazonium tars and tar-like polythiocompounds are produced, which do not readily undergo the chemical changes (as do the desired products identified above), to compounds such as 2,2'-dithiodibenzoic acid, and thus are useless but harmless by-products of the method of the instant invention. However, since these by-products are hydrolyzed to corresponding acids, elemental sulfur, and various polymers, it is desirable to use a procedure of carrying out the method which minimizes such contaminating by-products so that yields, for example, of 2,2'-dithiodibenzoic acid, are maximized. The procedures utilized in the examples following this discussion illustrate ways in which this may be accomplished.

Various factors and conditions influence the course of the coupling reaction between the diazonium salt and $CS_2$ and, in turn, the ratio of the desired products to undesirable by-products. Of these, the most important is the identity of the substituent R in the amine starting ingredient:

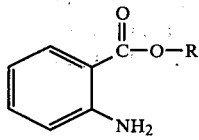

It has been discovered that higher yields of useful compounds are produced according to the method of the invention when R is methyl, ethyl, propyl or butyl. If R is hydrogen, aryl, aralkyl, or a branched or longer alkyl group, the composition of the reaction products of the coupling with $CS_2$ is shifted in favor of undesired by-products. Maximum yields have been achieved when R has been methyl or ethyl.

Electron-attracting groups, e.g., halogen and $NO_2$, as substituents on the benzene ring of the amine, severely decrease yields of useful compounds.

The acid used to perform diazotization of the amine influences to some degree the course of the subsequent $CS_2$ coupling. The maximum yield of useful coupling products has been obtained by the use of HCl; sulfuric acid has been found to encourage the formation of salicylic acid or its esters and is therefore less satisfactory for use in the method of the invention.

The availability of $CS_2$ for coupling with the diazonium is a critical factor in the desired execution of the reaction; an aqueous solution of diazonium compounds reacts very slowly with $CS_2$, even under the catalytic influence of copper or copper salts. The reaction between a diazonium salt and $CS_2$ occurs rapidly in the presence of a "helping" solvent, i.e., one which is water-miscible and in which the $CS_2$ is dissolved; the reaction proceeds, but only slowly, without the helping solvent. This is believed to indicate that the helping solvent makes the $CS_2$ available for reaction with diazonium.

Useful helping solvents have been found to include dioxane, dimethylformamide, dimethylsulfoxide, tetrahydrofurane, and water-miscible alcohols such as methanol, ethanol, n-propyl and isopropyl alcohol. For comparison, and to illustrate the importance of the identity of the helping solvent, several solvents were used in separate trials of the method of the instant invention; specifically, a 16.8 g portion of $CS_2$ was dissolved in 250 ml of each solvent, and the resulting solution of $CS_2$ was then reacted with an equimolecular quantity of a diazonium. The procedure described in EXAMPLE II, infra, was used in each case. The results obtained in the trails are summarized in the following table:

| Trial | Solvent (250 ml.) | Percent Yield* |
|---|---|---|
| 1. | Methanol | 89% |
| 2. | Isopropyl alcohol | 88% |
| 3. | n-Propyl alcohol | 87% |
| 4. | Dioxane | 82% |
| 5. | Dimethylsulfoxide/$H_2O$ (1:1 vol.) | 82% |
| 6. | Tetrahydrofurane | 82% |
| 7. | Dimethylformamide/$H_2O$ (1:1 vol.) | 60% |

*The reaction products were converted to 2,2'-dithiodibenzoic acid; percent yield refers to percent of expected yield of 2,2'-dithiodibenzoic acid, based on the weight of the diazonium reactant.

The quantity of helping solvent necessary to provide adequate availability of $CS_2$ for reaction with the diazonium is believed to be a function of the amount of water in the starting diazonium solution. In the best mode of carrying out the method of the invention, the ratio of solvent to the aqueous portion of the diazonium solution should be substantially 1.5:1. Although the coupling reaction proceeds at the fastest possible rate to the optimum yield of desired products when at least this amount of solvent is used, a decrease in this ratio to a level of 1.2:1 can be tolerated without serious detrimental effects (this level has been found to result in a decrease of about 25% in the rate of reaction). A ratio lower than 1.2:1 results in a much slower rate of reaction and as a consequence is economically unattractive. Conversely, a ratio of solvent to $H_2O$ greater than 1.5 to 1 offers no advantage but is not harmful to the reaction. However, separating an excessive quantity of solvent from the final reaction mixture requires more distillation time and processing expense.

It was found experimentally that the amount of $CS_2$ necessary to react fully with the diazonium salt is 1 gram-mole per gram-mole of diazonium. As illustrated in the examples, an excess of at least 10% $CS_2$ over this amount is preferred, however, as it is usually impossible to prevent losses due to the low boiling point of this compound: the ordinarily violent evolution of gas during coupling carries away $CS_2$, and only a partial recovery of vapors can be expected even when a reflux condenser cooled with ice-water is used.

The form of copper used to catalyze the coupling reaction is also important to the formation of desired products. Metallic copper, either in the form of copper bronze or in the form of copper coils formed of solid rods or tubing or copper sheet submerged in the reaction mixture, is preferred as the most efficient and practical catalyst. The use of copper salts, while theoretically possible, has been found to produce problems connected with recovery of this form of catalyst from the reaction mixture, and has also been found to be inferior in terms of results.

Metallic copper is a more efficient catalyst because the diazonium cation can accept an electron from the copper surface. A free phenyl-radical is formed, while the cuprous cation goes into the solution. At the end of the free-radical reaction the donated electron is recovered; it deionizes the cuprous cation and elemental copper is redeposited on the surface of the copper sheet. Only a small part of the regenerated copper stays suspended in the solution; it is later trapped in the separated product of the reaction. If, during the course of the reaction, the cuprous cation donates its second electron, later recovery of the electron might end in the formation of a cuprous cation, which stays in the solution. A large amount of cuprous cations might be expected to remain in the solution if a cuprous compound is initially used as the catalyst. As only a small amount of copper is lost from a mass of metallic copper catalyst, this type of material is desirable economically as well as technologically because of its recoverability.

Because the rate of the coupling reaction principally depends on the rate of transfer of electrons between the liquid phase and the surface of the copper catalyst, the success of the process depends first on the size, shape and microstructure of the exposed surface area of the catalyst and, secondly on other factors such as the rate and kind of agitation, the concentration of the reactants, the rate of separation of reaction products from the reaction mixture, the amount and type of helping solvents, and on various other factors which are evident in the examples following this discussion.

It has been found that approximately 0.05 mole of commerical copper bronze per gram-mole of diazonium solution adequately catalyzes coupling. In the case of the use of a copper mass such as copper sheet, coil or tubing, a surface area of at least 2000 square centimeters per gram-mole of diazonium reactant should be provided. From 2000 to 3000 square centimeters copper surface per gram-mole of diazonium is preferred. While an area greater than 3000 square centimeters offers no advantage, an area less than 2000 square centimeters can be used; however, a slowing-down of the reaction rate corresponding with decreased active Cu availability becomes more and more evident as the copper surface area is reduced, and the reaction is therefore economically less desirable.

The temperature of the reaction between a diazonium salt and $CS_2$, according to the method of the invention, should be in the range of 10°-32°. However, the reaction has been found to proceed most efficiently and with a minimum of by-product formation when the temperature is maintained between 28° and 30°. The time required for diazonium/$CS_2$ coupling has been found to be in the range of 20-45 minutes in the method of the invention when a batch process is used. However, since reaction time is a very abstract variable, which can vary within a very broad range depending on many factors, it is possible that the reaction under certain conditions may take only a few seconds as, for example, in a flow-through process. So long as diazonium/$CS_2$ coupling is proceeding at a substantial rate there is comparatively vigorous and visible evolution of $N_2$. Accordingly, it is preferred that the reaction be continued so long as vigorous gas evolution can be observed. Such a procedure assures maximum yields.

The product of the coupling reaction often appears in the reaction mixture in the form of orange-red colored sticky solids or of thick, deeply-colored oil. It has a tendency to adhere to the walls of the reaction vessel and to all other equipment used (the stirrer, the thermometer, etc.), including the surface of the copper catalyst. Because the helping solvent, at the end of the reaction, can hold in solution only a small quantity of reaction products, it has been found to be desirable to use another solvent to separate the product from the reaction equipment. Examples of solvents which can be used for this purpose are water-immiscible, inert solvents such as $C_6H_5Cl$, $C_6H_4Cl_2$ or $C_6H_3Cl_3$, all good solvents for the desired products.

In batch work this final solvent can be charged to the reaction vessel either at the end of the reaction of the diazonium solution with $CS_2$ or before the reaction commences. The latter charging, which offers no advantage for batch production, is usually applied in continuous-process operation to prevent deactivation of the copper by coating of the separated reaction product thereon.

Technical trichlorobenzene is an example of a high-boiling solvent that is preferably used for the following reasons:

a. The recovery of helping solvent from the mixed organic and aqueous phases by simple distillation is easier. For example, up to 85 percent of the original $CH_3OH$ charged can be recovered.
b. The eliminating of volatile impurities is facilitated. Such impurities as, for example, methyl benzoate are removed, if about ⅛ of the total volume of the trichlorobenzene is distilled off.
c. The solution of products in a high boiling solvent such as trichlorobenzene can conveniently be used in subsequent processes without the necessity of intermediate isolation of these products.
d. The recovery and recycling of this solvent after use is simple and practically quantitative.

Lower-boiling solvents such as, for example, ethylene dichloride, trichloroethane and the like can be used when the separation of the mixture into specified components by means of fractioned crystallization is desired.

The method of the instant invention is illustrated by the following examples which describe diazotizing an aromatic amine and coupling the resulting diazonium salt with carbon disulfide in the presence of a copper catalyst. The product of the coupling reaction is a mixture of a dithiodibenzoate, a dithiocarbonate, a trithiocarbonate and minor by-products. This reaction mixture can be hydrolyzed with a base and then oxidized to produce such compounds as 2,2'-dithiodibenzoic acid, or it can be converted to other useful products through other processes, the description of which is outside the scope of this invention.

EXAMPLE I (A) Diazotization of methyl anthranilate:

A diazonium solution was produced in a 600 ml beaker from 75.6 g methyl anthranilate, 220 ml 5 N HCl and a solution of 35 g sodium nitrite in 50 ml water. The beaker was equipped with a mechanical stirrer, a thermometer, an addition funnel and a cooling ice-salt bath. The beaker was charged with the methyl anthranilate and 110 ml water, and the contents were stirred. The HCl was then charged to the beaker in a single increment. The mixture was then cooled to about 0°–5°, and was diazotized by slowly adding the sodium nitrite solution over a period of 15 minutes. The temperature of the resulting diazonium solution was maintained at about 0°–5°.

(B) Coupling reaction between the diazonium salt solution (produced by diazotization of methyl anthranilate according to part A) and carbon disulfide in the presence of a copper powder catalyst:

The diazonium solution produced as described above was coupled in a 2 liter resin kettle with 41.9 g $CS_2$ in the presence of 1.6 g copper powder and 700 ml methanol. The kettle was equipped with a mechanical stirrer, a thermometer, an addition funnel and a reflux condenser cooled with ice-water, with a gas bubbler over its open end. The resin kettle was charged with the methanol, the $CS_2$ and the copper powder, and the mixture was stirred. After the mixture had been well agitated, the diazonium salt solution was gradually charged to the resin kettle in a total time of approximately 12 minutes; the temperature of the reaction mixture was maintained in the range of 28°–30° during coupling. After the last of the diazonium solution had been charged, the reaction mixture was stirred for thirty minutes, during which time evolution of $N_2$ ceased and a red oil separated from the mixture.

A 300 ml portion of trichlorobenzene was added to the reaction mixture and copper was removed from the resulting solution by filtration. The solution was then heated to a temperature of up to approximately 90° to remove the methanol by distillation. A charge of 400 ml of water was added to the hot reaction mixture in the flask. The mixture was then stirred, after which the lower trichlorobenzene layer was separated, and the upper aqueous phase was discarded.

The organic phase (trichlorobenzene layer), contained a mixture of dimethyl 2,2'-dithiodibenzoate, bis-(o-methoxycarbonylphenyl) trithiocarbonate, S,S-bis (o-methoxycarbonylphenyl) dithiocarbonate, and minor amounts of methyl benzoate and methyl o-clorobenzoate. The organic phase was then subjected to a vacuum distillation which reduced its volume by about one third. This partial distillation removed the methyl benzoate and other volatile products formed during the coupling reaction, leaving a mixture of a dithiodibenzoate and dithio-and trithiocarbonates.

EXAMPLE II (A) Diazotization of methyl anthranilate:

A diazonium solution was produced in a 600 ml beaker from 75.6 g methyl anthranilate, 100 ml concentrated HCl and a solution of 38 g sodium nitrite in 60 ml water. The beaker was equipped with a mechanical stirrer, a thermometer, two addition funnels and a cooling ice-salt bath. The beaker was charged with the methyl anthranilate and 110 ml water, and the contents were stirred. One of the addition funnels was charged with the concentrated HCl and the other was charged with the sodium nitrite solution. The stirred mixture in the beaker was then cooled to about 0°–10°, and was diazotized by charging the solutions of sodium nitrite and concentrated hydrochloric acid in the addition funnels into the beaker simultaneously, in the ratio of their volumes, over a period of about 20 minutes.

During diazotization the reaction mixture was rapidly stirred and the temperature of the mixture was maintained in the range of 0°–5°. The volume of the resulting diazonium salt solution was 270 ml.

(B) Coupling reaction between the diazonium salt solution (produced by diazotization of methyl anthranilate according to part A) and carbon disulfide in the presence of a solid copper mass (copper tubing) as a catalyst.

A 108 ml portion (0.2 gram-mole) of the diazonium solution produced as described above was coupled in a 500 ml resin kettle with 16.8 g $CS_2$, in the presence of copper tubing, 250 ml methanol and 50 ml trichlorobenzene. The kettle was equipped with a mechanical stirrer, a thermometer, an addition funnel, and a reflux condenser cooled with ice water with a gas bubbler over the open end. A coil made of ¼ inch copper tubing with an outside diameter smaller than the internal diameter of the resin kettle was inserted into the kettle, so that the copper surface immersed in and exposed to the reaction mixture was about 484 square centimeters (the open ends of the tubing were sealed so reacting liquid could not enter the interior of the coil).*

*This area corresponded to a surface area exposed to the reaction mixture of 2420 square centimeters per gram-mole of the diazonium.

The kettle was charged with the methanol, the $CS_2$, and the trichlorobenzene, and the mixture was stirred. After the mixture had been well agitated, the kettle was warmed to 30° and the diazonium salt solution was added to the mixture from the addition funnel in a total time of approximately 15 minutes; the temperature of the reaction mixture was maintained in the range of 29°–30° during coupling. After the last of the diazonium solution had been charged the reaction mixture was stirred for an additional 15 minutes, during which time evolution of $N_2$ ceased.

The copper tubing was removed from the reaction vessel and rinsed with a small amount of methanol. The reaction mixture was then heated to a temperature of up to approximately 78° to remove the methanol by distillation.

The resulting solution was cooled to about 40° and transferred to a separatory funnel. A charge of 100 ml water was added to the funnel, after which the organic phase (trichlorobenzene layer), containing the desired reaction products as in EXAMPLE I, was separated. The upper aqueous layer was washed with 50 ml of fresh trichlorobenzene; the trichlorobenzene layers were then combined and charged into a 300 ml flask, and the trichlorobenzene solution was subjected to a vacuum distillation, which reduced its volume by about one third. This partial distillation removed the methyl benzoate and other volatile products formed during the coupling reaction, leaving a mixture of products substantially identical to those of EXAMPLE I, but in approximately 36 percent greater proportion per unit volume of the reaction mixture than in EXAMPLE I.

The procedure of EXAMPLE II demonstrates the suitability of continuous-process use of a flow-through reactor in place of a batch-type process. The increased concentration of the diazonium solution of the EXAMPLE II process increases the reaction rate with $CS_2$ sufficiently to make such a continuous process feasible. Thus, the embodiment of the invention illustrated by this example is preferred over others from both a technical and economic standpoint, constituting the best presently known mode.

EXAMPLE III (A) Diazotization of propyl anthranilate:

A diazonium solution was produced in a 250 ml beaker from 17.92 g n-propyl anthranilate, 44 ml water, 44 ml 5N HCl, and a solution of 7.0 g sodium nitrite in 10 ml water. The beaker was equipped with a mechanical stirrer, a thermometer, two addition funnels, and an ice-salt bath for cooling. The beaker was charged with the propyl anthranilate, water, and HCl, and the resulting slurry of amine hydrochloride was stirred. The mixture was then cooled to about 0°–3° and the solution of sodium nitrite was slowly charged into the slurry over a period of 15 minutes. The solution was then warmed to about 15° and stirred for 5 minutes, after which it was filtered through activated charcoal to remove any trace impurities. The volume of the resulting diazonium salt solution was 175 ml.

(B) Reaction of the diazonium salt solution (produced by diazotization of propyl anthranilate according to part A) and carbon disulfide in the presence of a copper powder catalyst:

The diazonium solution produced as described above was coupled in a 500 ml three-neck flask with 8.4 g $CS_2$ in the presence of 0.32 g copper powder and 150 ml methanol. The flask was equipped with a mechanical stirrer, a thermometer, an addition funnel and a reflux condenser cooled with ice water with a gas bubbler over its open end. The flask was charged with the $CS_2$, the methanol and the copper powder, and the mixture was stirred. After the mixture had been well agitated, the diazonium salt solution was gradually charged into the mixture in the flask over a period of about 20 minutes; the contents of the flask were warmed from about 10° to 30° during coupling. After the last of the diazonium solution had been charged, the reaction mixture was transferred to a 1 liter flask and the methanol was stripped off.

The remaining solution in the flask was then quenched into 400 ml water, whereupon a red oil separated from the mixture. The oil was dissolved by adding 45 ml trichlorobenzene, after which the trichlorobenzene (organic) layer which formed was separated from the aqueous layer. Metallic copper was separated from the trichlorobenzene layer by filtration, after which the filtrate was transferred to a 300 ml three-neck flask. The separated trichlorobenzene layer contained a mixture of compounds of the types described in EXAMPLES I and II.

EXAMPLE IV

The procedure described in EXAMPLE III was used to diazotize 16.52 g ethyl anthranilate, with the exception that, after cooling of the amine hydrochloride slurry, 50 ml of 2 N sodium nitrite (replacing the $NaNO_2$ solution of EXAMPLE III) was gradually added to the reaction mixture in the beaker while the temperature of the solution was maintained between 0° and 10°. The diazonium salt solution obtained was then coupled with $CS_2$ by substantially the procedure described in EXAMPLE III to produce the same types of compounds.

EXAMPLE V

The procedure described in EXAMPLE IV was used to diazotize 19.32 g isobutyl anthranilate. The diazonium salt solution obtained was coupled with $CS_2$ by substantially the procedure described in EXAMPLE III, with the exception that an additional 100 ml methanol was added during the charging of the diazonium to compensate for early separation of the red oil from the reaction mixture. The same types of compounds were produced by the coupling reaction as in the previous examples; however, greater contamination of the product by the undesirable by-products previously identified was found to occur than under the procedures of the previous examples, resulting in substantially lower yields of these compounds.

EXAMPLE VI

The procedure described in EXAMPLE V was used to diazotize 19.32 g n-butyl anthranilate. The diazonium salt solution obtained was coupled with $CS_2$ by substantially the procedure described in EXAMPLE V to produce the same types of compounds as in the previous examples.

Stoichiometrically identical quantities of sec-butyl anthranilate, anthranilic acid, and isopropyl anthranilate were respectively diazotized as described in EXAMPLE V. The diazonium salt solutions obtained were thereafter each coupled with $CS_2$ by substantially the procedure described in EXAMPLE V. However, the reactions were found to be each shifted in favor of undesirable by-products, resulting in substantially lower yields of the desired coupling products previously described.

As the presence of copper catalyzes the $CS_2$ coupling reaction described in the foregoing EXAMPLES by means of an electron-transfer process, a copper sheet can be used to supply electrons to the diazonium cations, in place of the copper powder or tubing described. The surface of exposed copper metal should be equal at least 2000 square centimeters per gram-mole of the diazonium reactant to provide the requisite electron transfer and enable the reaction to proceed at a resonable rate. A surface area in the range of 2500 to 3000 square centimeters of copper per gram-mole of diazonium is preferred. A greater copper surface area, while not detrimental to successful coupling, is not needed and is usually an unnecessary expense.

Although preferred embodiments of the method of the instant invention have been described, the preceding examples are merely illustrative and not exhaustive and it will be apparent that various changes and modifications can be made from the specific disclosures hereof without departing from the spirit and scope of the invention as defined in the following claims.

What I claim is:

1. A method for producing a dithiodibenzoate, dithiocarbonate, trithiocarbonate mixture, comprising the steps of diazotizing an amine having the formula

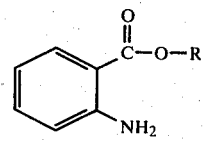

where R is hydrogen, or an alkyl group having not more than 4 carbon atoms, and reacting with each gram-mole of the resulting diazonium at least 1 gram-mole of carbon disulfide dissolved in a water-miscible solvent in the presence of copper having a surface area of at least 2000 square centimeters, at a temperature within the range of 10°–32° and for a period of time sufficient to produce said mixture.

2. The method of claim 1 wherein R is methyl.

3. The method of claim 1 wherein the copper is in the form of a powder.

4. The method of claim 1 wherein the copper is in the form of tubing.

5. The method of claim 1 wherein the copper has a surface area of from 2500–3000 square centimeters per gram-mole of the diazonium.

6. The method of claim 1 wherein the solvent is methanol.

7. The method of claim 1 wherein the carbon disulfide is dissolved in the solvent before the reaction of the diazonium therewith.

8. The method of claim 1 wherein the products of the reaction are dissolved and removed from the system by means of a water-immiscible, inert solvent.

9. The method of claim 8 wherein the solvent is added during the reaction of the diazonium with carbon disulfide.

10. The method of claim 8 wherein the solvent is selected from the group consisting of chlorobenzene, dichlorobenzene, trichlorobenzene, ethylene dichloride and trichloroethane.

11. The method of claim 8 wherein the solvent is added before the reaction of the diazonium with carbon disulfide.

12. The method of claim 8 wherein the solvent is added at the end of the reaction of the diazonium with carbon disulfide.

13. The method of claim 1 wherein the copper is in the form of sheet.

* * * * *